United States Patent [19]
Huzinec et al.

[11] Patent Number: 4,681,766
[45] Date of Patent: Jul. 21, 1987

[54] COATINGS FOR CHEWING GUMS CONTAINING GUM ARABIC AND A SOLUBLE CALCIUM SALT

[75] Inventors: Robert J. Huzinec, Kenvil; Allan H. Graff, Randolph, both of N.J.

[73] Assignee: Warner-Lambert Company, Morris Plains, N.J.

[21] Appl. No.: 816,762

[22] Filed: Jan. 7, 1986

[51] Int. Cl.⁴ ............................................. A23L 1/09
[52] U.S. Cl. ........................................ 426/5; 426/103; 426/302; 426/310; 426/658
[58] Field of Search ........................................ 426/3-6, 426/302, 303, 307, 310, 97, 103, 658

[56] References Cited

U.S. PATENT DOCUMENTS

| | | | |
|---|---|---|---|
| 2,304,246 | 12/1942 | Ekert | 426/5 |
| 3,456,050 | 7/1969 | Rieckmann et al. | 426/5 |
| 4,238,510 | 12/1980 | Cherukuri et al. | 426/5 |
| 4,317,838 | 3/1982 | Cherukuri et al. | 426/5 |

OTHER PUBLICATIONS

Little et al., Tablet Making, "Pan Coating" Northern Pub. Co. Ltd., England, 1949, pp. 103–104.

Primary Examiner—Jeanette Hunter
Attorney, Agent, or Firm—Daniel A. Scola, Jr.; Henry C. Jeanette; Gary M. Nath

[57] ABSTRACT

The invention provides a method for coating comestibles such as chewing gum and candy with sugarless and sugar coatings from aqueous syrups containing a sweetener, gum arabic and a calcium salt, preferably calcium chloride, which coatings are smooth and non-flaky and crunchy when chewed.

21 Claims, No Drawings

COATINGS FOR CHEWING GUMS CONTAINING GUM ARABIC AND A SOLUBLE CALCIUM SALT

This invention relates to sugar and sugarless coatings containing gum arabic for comestibles such as chewing gums, confections or pharmaceutical preparations and tablets. More particularly the invention is concerned with smooth and non-flaking sugar and sugarless coatings for comestibles made from coating syrups containing gum arabic and calcium chloride. These coatings are intended to be hard or crunchy in nature of the type commonly known in the pellet gums, e.g. CHICLET brand gum.

In the past, chewing gums in the form of shaped centers or cores, e.g. pellet gums, have been coated both with sugar and sugarless coatings to produce a candy-like, crunchy outer taste in the mouth with a chewable gum center portion. Conventionally, the core is a soft chewing gum portion, whereas the coating is crunchy or hard. In the case of sugarless coatings, aqueous solutions of xylitol, mannitol, maltitol and sorbitol, known as syrups, have been primarily employed. Such syrups may contain additives such as moisture absorbing compounds, anti-adherent compounds, dispersing agents, film forming agents, binders and the like. Binders are particularly useful in that they aid in initially binding the sweetener to the gum core or center being coated. Gum arabic, commonly used as a binder, is a natural gum obtained from the stem and branches of acacia Senegal and related species of acacia. It has an estimated molecular weight of between 241,000 and 500,000 and is composed of arabinose, galactose, rhamnose, and glycuronic acid.

In U.S. Pat. No. 4,307,838 a method for forming a sugarless coating on centers of chewing gum or other comestibles is described which includes the steps of applying to the centers a coating syrup which contains a sweetener such as sorbitol and/or other non-sugar sweetener, an adhesion or binder component such as gum arabic and a film forming component, an anti-adherent or filler component, and a dispersing agent to thereby coat the centers with the coating syrup, and then applying a dusting mix to the centers coated with the coating syrup, the dusting mix including one or more sweeteners, such as employed in the coating syrup, in powdered form, and a moisture absorbing component, an anti-adherent component and a dispersing agent. See also UK Patent Application GB 2079129A which describes a similar method which further comprises applying a second coating syrup to smooth out the coating of the centers and provides a shine thereto, which second coating generally includes ingredients similar to those present in the dusting mix but dispersed in water.

One of the problems associated with forming coatings from these syrups is lumping and flaking of the finished coating rendering them unacceptable. The prior art has failed to disclose an effective coating or process to remedy this problem.

The present invention, on the other hand, employs a water soluble calcium salt such as calcium chloride in solution with the gum arabic and sweetener to provide uniform, smooth, and non-flaky coatings on comestible shapes, particularly chewing gum. The coatings must be resistant to enbrittlement, e.g., be flexible, yet have a hard crunchy bite. Although the mechanism is not precisely known it is believed that the calcium from the calcium salt reacts with one or more free carboxylic acid groups of the gum arabic to form a product which aids in developing a film around the gum center or core so that additional coats of sweetener may be added. This product assists in forming a smooth, hard finished coating and also helps the coating adhere to the shape to prevent flaking. It has been found that other water soluble divalent metal salts such as magnesium chloride and zinc chloride to not produce non-flaky coatings with gum arabic and are therefore unsuitable in the present invention.

In accordance with the invention an improved method is provided for forming a sugar or sugarless coating on a solid shape of chewing gum or other comestible which comprises applying to the shape a coating syrup which contains a sweetener, gum arabic and a water soluble calcium salt. The application of the coating syrup can be repeated, as many times as necessary to build up a desired coating weight and thickness on the shape.

For purposes of this invention, the term "comestible" is meant to include chewing gums, pharmaceutical preparations, confectionery products such as mints, lozenges, nougats and a wide variety of other solid or semi-solid edible products.

In carrying out the method of the invention, the coating syrup will be formed as an aqueous solution of the sweetener, the gum arabic binder, water-soluble calcium salt and other additives, if desired.

The sweetener may be present in an amount of from about 30% to about 80% by weight of the coating syrup and preferably from about 40% to about 60% by weight. The gum arabic should be present in an amount of from about 1% to about 15% by weight of the coating syrup and preferably from 5% to about 10% by weight. The water soluble calcium salt should be present in an amount of from about 0.05% to about 10% by weight of the gum arabic and preferably from about 3% to about 8% by weight with the remainder being water and minor amounts of optional additives, if employed.

Calcium chloride is the preferred water soluble calcium salt for use in the invention due to its high solubility and availability. However other water soluble calcium salts such as calcium bromide, calcium iodide, calcium nitrate, calcium nitrite, calcium maleate, calcium butyrate, calcium isobutyrate, calcium hypochlorite and mixtures thereof may also be employed.

The sweeteners suitable for use in the coating syrup comprise sugarless sweeteners such as the polyhydric alcohols, e.g., xylitol, sorbitol, mannitol, and mixtures, thereof, with xylitol being preferred; as well as maltitol, isomaltitol, hydrogenated starch hydrolysates, and hydrogenated glucose syrups. Mono, di- and polysaccharide may also be included. For example, sugars such as sucrose, fructose, glucose, galatose and maltose may also be employed as a sweetener. Other sweeteners suitable for use in the coating syrup include, but are not limited to free saccharin acid, water soluble salts of saccharin, cyclamate salts, palatinint dihydrochalcones, glycyrrhizin, L-aspartyl-L-phenylalanine methyl ester, amino acid based sweeteners, talin, steviosides, dihydrochalcone compounds, acesulfame salts and mixtures thereof.

Other components may be added in minor amounts to the coating syrup and include moisture absorbing compounds, anti-adherent compounds, dispersing agents and film forming agents.

The moisture absorbing compounds suitable for use in the coating syrups include mannitol or dicalcium phosphate. Examples of useful anti-adherent compounds, which may also function as a filler, include talc, magnesium trisilicate and calcium carbonate. These ingredients may be employed in amounts of about 0.5% to about 5% by weight of the syrup.

Examples of dispersing agents which may be employed in the coating syrup include titanium dioxide, talc or other anti-adherent compounds as set forth above.

The coatings from the coating syrup are preferably applied by pan coating, although other conventional techniques may be useful. In pan coating methods, chewing gum pellet cores or other shapes are placed in a revolving coating pan and dedusted using cool dry air. The coating syrup is heated to about 50° C. to 60° C. and a portion thereof added to the revolving pan. Generally a single deposition of the coating syrup is not sufficient to provide the desired amount or thickness of coating deposited on the comestible. Accordingly, it usually will be necessary to apply second, third or more coats of the coating syrup in order to build up the weight and thickness of the coating to desired levels. However, before applying subsequent layers of the coating syrup, the previously applied layers are allowed to dry by gently flowing warm air or by adding a drying agent such as calcium carbonate or sorbitol in the case of sugarless coatings, or powdered sugar in the case of sugar coatings. Thereafter an additional portion of syrup is added followed by drying with air or drying agent and this procedure is repeated until the desired coating weight is obtained. For example, in coating chewing gum, the applications of coating syrup are continued until the average gum piece weight reaches the required coating weight. Thus, if the coating is to comprise about 35% by weight of the coated chewing gum tablet, application of 6 to 12 coats of coating syrup may be required. Other types of syrups may be added between portions of the inventive coating syrup such as an aqueous xylitol, maltitol or sorbitol solution in the case of sugarless coatings or a sugar solution in the case of sugar coatings. A flavorant such as peppermint oil, spearmint oil or the like may also be added. The distribution time, that is, the time during which the syrup or drying agent is mixed with the shapes is usually from 1 to 3 minutes. After the desired weight of coating has been obtained the coated shapes are dried with cool air (10°-16° C.).

In the case where the comestible to be coated is chewing gum, flavoring and other conventional additives may be added to the gum base. Such flavoring may comprise oils derived from plants, leaves, flowers, fruit etc. Representative flavor oils of this type include citrus oils such as lemon oil, orange oil, lime oil, grapefruit oil, fruit essences such as apple essence, pear essence, peach essence, strawberry essence, apricot essence, raspberry essence, cherry essence, plum essence, pineapple essence, as well as the following essential oils: peppermint oil, spearmint oil, mixtures of peppermint oil and spearmint oil, clove oil, bay oil, anise oil, eucalyptus oil, thyme oil, cedar leaf oil, cinnamon oil, oil of nutmeg, oil of sage, oil of bitter almonds, cassia oil, and methylsalicylate (oil of wintergreen). Various synthetic flavors such as mixed fruit, may also be incorporated.

Sweeteners suitable for use herein which may be present in the gum center and/or coating may comprise natural or synthetic sugar substitutes. Examples of synthetic sweeteners suitable for use herein include free saccharin acid, sodium, calcium or ammonium saccharin, cyclamate salts, dihydrochalcones, glycyrrhizic acid and salts, L-aspartyl-L-phenylalanine methyl ester, the sodium or potassium salt of 3,4-dihydro-6-methyl-1,2,3-oxathiazine-4-one-2,2-dioxide (Acesulfame), steviosides, dihydrochalcone compounds and mixtures thereof.

Where employed, natural sugars and/or natural sugar substitutes may be present in the chewing gum center. Such natural sweeteners suitable for use herein include polyhydric alcohols, such as sorbitol, xylitol, mannitol, isomaltitol, or maltitol. If desired, sugars such as mono-, di- and polysaccharides may also be employed. Representative examples include sucrose, dextrose, maltitose, fructose, maltodextrin, lactose and the like.

In general, the gum base is prepared by heating and blending various ingredients, such as natural gums, synthetic resin, waxes, plasticizers, etc, in a manner well known in the art. Typical examples of the ingredients found in a chewing gum base are masticatory substances of synthetic origin such as styrene-butadiene copolymer, isobutylene-isoprene copolymer, polyisobutylene, polyethylene, petroleum wax, polyvinyl acetate, as well as masticatory substances of natural origin such as rubber latex solids, chicle, crown gum, mispero, rosidinha, jelutong, pendare, perillo, niger gutta, tunu, etc. The elastomer or masticatory substance will be employed in an amount within the range of about 5 to about 15%, preferably from about 8 to 12%, and optimally from about 9 to about 11% by weight of the chewing gum composition.

The gum base may also include solvents, detackifiers, waxes, softening agents, lubricants, fillers, emulsifiers, colorants, antioxidants and/or texturizers, bulking agents and other conventional ingredients as will be apparent to those skilled in the art.

As indicated, in addition to chewing gum, the comestible to be coated may include any edible solid, such as candies, including hard candies and pressed candies, jelly beans, peanuts, other confections, as well as pharmaceutical preparations including pills, tablets or other solid dosage forms for medicinal or therapeutic use.

By employing the inventive syrup as the initial coating medium for comestibles such as gum, confectionery and pharmaceutical dosage forms, smooth and non-flaky coatings are produced. In experiments employing coating syrups containing a sweetener, gum arabic but no water soluble calcium salt the resulting coatings were found to have a lumpy and irregular surface contour. Additionally, these coatings were brittle and peeled or flaked off causing an undesirable and ineffective coating.

In order to more completely describe the invention the following Examples are submitted, it being understood that such Examples are not intended to limit the scope of the invention. Percentages are by weight unless otherwise indicated.

EXAMPLE 1

This example demonstrates the preparation of a sugarless coating on a sugarless chewing gum center according to the invention which coating is both flexible, crunchy, yet non-flaking.

A sheet of gum centers or cores was prepared for all Examples herein from the ingredients set forth in Table 1 below.

TABLE 1

| Ingredient | wt. % |
|---|---|
| Gum Base (styrene butadiene) | 27.21 |
| Sorbitol (granular) | 21.00 |
| Glycerin | 5.23 |
| Sorbitol (solution) | 12.56 |
| Sorbitol (powder) | 32.40 |
| Flavorant (peppermint oil) | 1.60 |
| | 100.00 |

To prepare the centers, the gum base was melted and maintained at elevated temperatures. The glycerin was added followed by the solid sorbitols (granular and powder) which were added slowly with mixing. Thereafter the sorbitol solution was added followed by the flavor oil. The above mixture was mixed until homogeneous, cooled, rolled into sheets and scored to form a sheet of pillow shaped gum centers or cores.

A coating syrup (Syrup #1) was prepared by combining 171 g of a gum arabic/calcium chloride solution comprising 100 g of gum arabic, 11 g of calcium chloride and 200 g of $H_2O$ with 400 g of a xylitol solution comprising 390 g of xylitol and 110 g of $H_2O$ (78% xylitol solution). Syrup #1 had the composition as set forth in Table 2 below.

TABLE 2

| Ingredient | Wt. (g) |
|---|---|
| Gum Arabic | 55 |
| Xylitol | 312 |
| Calcium Chloride | 6 |
| $H_2O$ | 198 |
| | 571 g |

The gum centers to be coated were placed in sheet form in a standard revolving coating pan and were broken up into individual centers. The centers were dedusted using cool dry air. Syrup #1 was heated to 50°–52° C. The centers were coated six (6) times with Syrup #1 according to the scheme of Table 3 below. The 78% aqueous xylitol solution was also used as a coating syrup. Calcium carbonate was employed as a drying agent between charges of Syrup #1 and the 78% xylitol solution. Table 3 lists the charge sequence, the material applied, weight of material in grams and the distribution time in minutes in the pan coating apparatus.

TABLE 3

| Charge | Material Applied | Wt. Material (g) | Distribution Time (min) |
|---|---|---|---|
| 1 | Coating Syrup #1 | 30 | 1½ |
| 2 | CaCO₃ | 30 | 1½ |
| 3 | CaCO₃ | 30 | 1 |
| 4 | Coating Syrup #1 | 30 | 1 |
| 5 | CaCO₃ | 30 | 2 |
| 6 | CaCO₃ | 30 | 1 |
| 7 | 78% Xylitol Solution | 30 | 1½ |
| 8 | CaCO₃ | 30 | 2 |
| 9 | Coating Syrup #1 | 30 | 1 |
| 10 | CaCO₃ | 30 | 2 |
| 11 | CaCO₃ | 30 | 2 |
| 12 | 78% Xylitol Solution | 30 | 1½ |
| 13 | CaCO₃ | 30 | 2 |
| 14 | Coating Syrup #1 | 30 | 1 |
| 15 | CaCO₃ | 30 | 2 |
| 16 | CaCO₃ | 30 | 2 |
| 17 | 78% Xylitol Solution | 25 | 1½ |
| 18 | CaCO₃ | 30 | 2 |
| 19 | Coating Syrup #1 | 30 | 1½ |
| 20 | CaCO₃ | 30 | 2 |
| 21 | CaCO₃ | 30 | 2 |
| 22 | 78% Xylitol Solution | 30 | 1½ |
| 23 | CaCO₃ | 30 | 2 |
| 24 | Coating Syrup #1 | 30 | 1 |
| 25 | CaCO₃ | 30 | 2 |
| 26 | CaCO₃ | 30 | 2 |
| 27 | 78% Xylitol Solution | 35 | 2 |
| 28 | CaCO₃ | 30 | 2 |
| 29 | 78% Xylitol Solution | 35 | 2 |
| 30 | 78% Xylitol Solution | 35 | 2 |
| 31 | CaCO₃ | 30 | 2 |
| 32 | 78% Xylitol Solution | 35 | 2 |
| 33 | 78% Xylitol Solution | 35 | 2 |
| 34 | CaCO₃ | 30 | 2 |
| 35 | 78% Xylitol Solution | 35 | 2 |
| 36 | 78% Xylitol Solution | 35 | 3 |

The coated centers were then dried at 16° C. for three minutes. The coatings were smooth, non-flaky and crunchy when chewed. The resultant gum pieces were conditioned for 48 hours at ambient temperatures.

EXAMPLE 2

This Example demonstrates that xylitol coatings from syrups containing gum arabic without a water soluble calcium salt are unsatisfactory.

A 33% by weight gum arabic solution and a 78% xylitol solution was first prepared. A second crystalline coating syrup (Coating Syrup #2) was prepared from these solutions comprising 30 wt.% gum arabic solution and 70 wt.% xylitol solution. A third crystalline coating syrup (Coating Syrup #3) was prepared having the composition set forth in Table 4 below.

TABLE 4

| Ingredient | Wt. (g) |
|---|---|
| Gum Arabic | 40 |
| Xylitol | 780 |
| TiO₂ | 3 |
| $H_2O$ | 179 |
| Total | 1002 g |

The gum centers were pan coated in accordance with the general procedure of Example 1. The resultant pellet shaped chewing gum pieces were conditioned for 48 hours at ambient temperatures. Table 5 below summarizes the coating scheme.

TABLE 5

| Charge | Material Applied | Wt. Material (g) | Distribution Time (min) |
|---|---|---|---|
| 1 | Coating Syrup #2 | 25 | 2 |
| 2 | CaCO₃ | 50 | 2 |
| 3 | CaCO₃ | 50 | 2 |
| 4 | Coating Syrup #2 | 30 | 1 |
| 5 | CaCO₃ | 50 | 2 |
| 6 | CaCO₃ | 50 | 2 |
| 7 | Coating Syrup #2 | 30 | 1 |
| 8 | CaCO₃ | 50 | 2 |
| 9 | CaCO₃ | 50 | 2 |
| 10 | Coating Syrup #3 | 50 | 1 |
| 11 | CaCO₃ | 50 | 2 |
| 12 | CaCO₃ | 50 | 2 |
| 13 | Coating Syrup #3 | 25 | 1 |
| 14 | Coating Syrup #3 | 25 | 1 |
| 15 | Coating Syrup #3 | 25 | 2 |
| 16 | Coating Syrup #3 | 30 | 2 |

After drying lumps and irregular surface contours were present on the coating. The coating could be easily peeled off the gum center and was unsatisfactory in overall quality.

EXAMPLE 3

This Example further demonstrates the inferiority of xylitol coatings made from a syrup containing gum arabic and without a water soluble calcium salt.

Syrup #2 was employed in the pan coating of gum base centers according to the scheme of Table 6. In charge No. 7 & 15 a 33% gum arabic solution was itself used as a flexible coating.

TABLE 6

| Charge | Material Applied | Wt. Material (g) | Distribution Time (min) |
|---|---|---|---|
| 1 | Coating Syrup #2 | 30 | 2 |
| 2 | CaCO$_3$ | 20 | 1 |
| 3 | Coating Syrup #2 | 30 | 1 |
| 4 | CaCO$_3$ | 25 | 1 |
| 5 | Coating Syrup #2 | 30 | 1 |
| 6 | CaCO$_3$ | 25 | 1 |
| 7 | 33% Gum Arabic Solution | 20 | 1 |
| 8 | CaCO$_3$ | 30 | 2 |
| 9 | Coating Syrup #2 | 30 | 1 |
| 10 | CaCO$_3$ | 25 | 2 |
| 11 | CaCO$_3$ | 25 | 1 |
| 12 | Coating Syrup #2 | 30 | 1 |
| 13 | CaCO$_3$ | 25 | 1 |
| 14 | CaCO$_3$ | 25 | 1 |
| 15 | 33% Gum Arabic Solution | 20 | 1 |
| 16 | CaCO$_3$ | 30 | 2 |
| 17 | Coating Syrup #2 | 30 | 1 |
| 18 | CaCO$_3$ | 25 | 1 |
| 19 | CaCO$_3$ | 25 | 2 |
| 20 | Coating Syrup #2 | 60 | 1 |
| 21 | CaCO$_3$ | 60 | 1 |
| 22 | CaCO$_3$ | 70 | 2 |

After 5 minutes of air drying the coatings were found to be smooth but subsequent to conditioning for 48 hours at ambient temperature were found to be brittle and easily flaked off.

What is claimed is:

1. An aqueous coating syrup for use in coating chewing gums comprising:
   (a) from about 30% to about 80% by weight of the coating syrup of a sweetener;
   (b) from about 1% to about 15% by weight of the coating syrup of gum arabic; and
   (c) from about 0.05% to about 10% by weight of the gum arabic of a water soluble calcium salt selected from the group consisting of calcium chloride, calcium bromide, calcium iodide, calcium nitrate, calcium nitrite, calcium maleate, calcium butyrate, calcium isobutyrate, calcium hypochlorite and mixtures thereof.

2. The syrup of claim 1 wherein said comestible is chewing gum.

3. The syrup of claim 1 wherein said sweetener is a sugar alcohol selected from the group consisting of xylitol, sorbitol, mannitol and mixtures thereof.

4. The syrup of claim 1 wherein said sweetener is a sugar selected from the group consisting of sucrose, fructose and maltose.

5. The syrup of claim 1 wherein said water soluble calcium salt is calcium chloride.

6. The syrup of claim 1 wherein said sweetener comprises from about 40% to about 60% by weight of said syrup.

7. The syrup of claim 1 wherein said gum arabic comprises from about 5% to about 10% by weight of the coating syrup.

8. The syrup of claim 1 wherein said water soluble calcium salt comprises from about 3% to about 8% by weight of said gum arabic.

9. Chewing gums coated with the syrup of claim 1.

10. Chewing gums coated with the syrup of claim 3.

11. Chewing gums coated with the syrup of claim 5.

12. A method for preparing coated shaped chewing gums which comprises the steps of applying to said shaped chewing gums a coating syrup comprising an aqueous solution of about 30% to about 80% by weight of the coating syrup of a sweetener, about 1% to about 15% by weight of the coating syrup of gum arabic and about 0.05% to about 10% by weight of the gum arabic of a water soluble calcium salt selected from the group consisting of calcium chloride, calcium bromide, calcium iodide, calcium nitrate, calcium nitrite, calcium maleate, calcium butyrate, calcium isobutyrate, calcium hypochlorite and mixtures thereof and drying said syrup.

13. The method of claim 12 wherein said sweetener is a sugar alcohol selected from the group consisting of xylitol, sorbitol, mannitol and mixtures thereof.

14. The method of claim 12 wherein said water soluble calcium salt is calcium chloride.

15. A method for preparing a sugarless coating on chewing gums which comprises the steps of applying to said chewing gums a coating syrup comprising an aqueous solution of from 30% to 80% by weight of said syrup of a sugar alcohol selected from the group consisting of xylitol, sorbitol, mannitol and mixtures thereof, from 1% to 15% by weight of said syrup of gum arabic and from 0.05% to 10% by weight of said gum arabic of calcium chloride, and drying said syrup.

16. The method of claim 15 wherein the comestible is a chewing gum.

17. A chewing gum product having an inner core and a dry hard outer coating wherein the inner core comprises a gum base and the outer coating comprises about 30% to about 80% by weight of a sweetener, about 1% to about 15% by weight of gum arabic and about 0.05% to about 10% by weight of a water soluble calcium salt selected from the group consisting of calcium chloride, calcium bromide, calcium iodide, calcium nitrate, calcium nitrite, calcium maleate, calcium butyrate, calcium isobutyrate, calcium hypochlorite and mixtures thereof.

18. The product of claim 17 wherein the chewing gum base contains an elastomer selected from the group consisting of styrene-butadiene copolymer, isobutylene-isoprene copolymer, polyisobutylene, polyethylene, petroleum wax, polyvinyl acetate, rubber latex solids, chicle, crown gum, mispero, rosidinha, jelutong, pendare, perillo, niger gutta, tunu and mixtures thereof.

19. The product of claim 17 wherein the chewing gum base contains a flavorant selected from the group consisting of lemon oil, orange oil, lime oil, grapefruit oil, apple essence, pear essence, peach essence, strawberry essence, apricot essence, raspberry essence, cherry essence, plum essence, pineapple essence, peppermint oil, spearmint oil, clove oil, bay oil, anise oil, eucalyptus oil, thyme oil, cedar leaf oil, cinnamon oil, oil of nutmeg, oil of sage, oil of bitter almonds, cassia oil, methylsalicylate and mixtures thereof.

20. The product of claim 17 wherein the chewing gum base contains a sweetener selected from the group consisting of free saccharin acid, saccharin salts, cyclamate salts, dihydrochalcones, glycyrrhizic acid, glycyrrhizic salts, L-aspartyl-L-phenylalanine methyl ester, salts of 3,4-dihydro-6-methyl-1,2,3-oxathiazine-4-one- 2,2-dioxide, steviosides, dihydrochalcone compounds, polyhydric alcohols, mannitol, isomaltitol, maltitol, sucrose, dextrose, maltitose, fructose, maltodextrin, lactose and mixtures thereof.

21. The product of claim 17 wherein the chewing gum base contains a component selected from the group consisting of solvents, detackifiers, waxes, softening agents, lubricants, fillers, emulsifiers, colorants, antioxidants, texturizers, bulking agents and mixtures thereof.

* * * * *